(12) United States Patent
Heinrich et al.

(10) Patent No.: US 8,002,788 B2
(45) Date of Patent: Aug. 23, 2011

(54) TWO-MODE BLADELESS TROCAR ASSEMBLY

(75) Inventors: Russell Heinrich, Madison, CT (US);
David C. Racenet, Litchfield, CT (US);
Robert C. Smith, Middletown, CT (US);
Gregory G. Okoniewski, North Haven, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 244 days.

(21) Appl. No.: 12/244,150

(22) Filed: Oct. 2, 2008

(65) Prior Publication Data
US 2009/0093835 A1 Apr. 9, 2009

Related U.S. Application Data

(60) Provisional application No. 60/997,774, filed on Oct. 5, 2007.

(51) Int. Cl.
*A61B 17/00* (2006.01)
(52) U.S. Cl. ........................................ 606/190; 600/184
(58) Field of Classification Search .................. 606/185, 606/190; 604/170.02; 600/184
See application file for complete search history.

(56) References Cited

U.S. PATENT DOCUMENTS

| | | | |
|---|---|---|---|
| 4,535,773 A | 8/1985 | Yoon | |
| 4,601,710 A | 7/1986 | Moll et al. | |
| 4,654,030 A | 3/1987 | Moll et al. | |
| 4,902,280 A | 2/1990 | Lander | |
| 4,931,042 A | 6/1990 | Holmes et al. | |
| 5,030,206 A | 7/1991 | Lander | |
| 5,066,288 A | 11/1991 | Deniega et al. | |
| 5,104,382 A | 4/1992 | Brinkerhoff et al. | |
| 5,114,407 A | 5/1992 | Burbank | |
| 5,116,353 A | 5/1992 | Green | |
| 5,152,754 A | 10/1992 | Plyley et al. | |

(Continued)

FOREIGN PATENT DOCUMENTS

EP 0 604 197 A2 12/1993

(Continued)

OTHER PUBLICATIONS

European Search Report for corresponding EP 08253235 date of mailing is Mar. 24, 2010 (3 pages).

*Primary Examiner* — Victor Nguyen

(57) ABSTRACT

An obturator assembly for penetrating tissue and being at least partially positionable within a cannula assembly includes an obturator housing, an obturator shaft connected to the obturator housing and defining a longitudinal axis, a bladeless penetrating member adjacent the distal end of the obturator shaft and an obturator shield mounted about the obturator shaft and having a distal shield nose. The obturator shield is adapted for longitudinal movement between an extended position where the bladeless penetration member is substantially enclosed within the shield nose and a retracted position where the bladeless penetrating member is at least partially exposed from the shield nose. A manually manipulative member is mounted to the obturator housing and is adapted for rotational movement about the longitudinal axis and relative to the obturator housing between an initial position corresponding to a first mode of operation where the obturator shield is secured in the extended position and the shield nose is used to penetrate tissue, and a release position corresponding to a second mode of operation operatively releasing the obturator shield to permit the obturator shield to move to the retracted position thereof to expose the bladeless penetrating member for further dissecting the tissue.

13 Claims, 12 Drawing Sheets

U.S. PATENT DOCUMENTS

| | | | |
|---|---|---|---|
| 5,158,552 A | 10/1992 | Borgia et al. |
| 5,215,526 A | 6/1993 | Deniega et al. |
| 5,226,426 A | 7/1993 | Yoon |
| 5,246,425 A | 9/1993 | Hunsberger et al. |
| 5,248,298 A | 9/1993 | Bedi et al. |
| 5,263,937 A | 11/1993 | Shipp |
| 5,275,583 A | 1/1994 | Crainich |
| 5,290,243 A | 3/1994 | Chodorow et al. |
| 5,295,993 A | 3/1994 | Green |
| 5,312,354 A | 5/1994 | Allen et al. |
| 5,314,417 A | 5/1994 | Stephens et al. |
| 5,318,580 A | 6/1994 | Gresl, Jr. |
| 5,318,585 A | 6/1994 | Guy et al. |
| 5,338,305 A | 8/1994 | Plyley et al. |
| 5,346,459 A | 9/1994 | Allen |
| 5,350,393 A | 9/1994 | Yoon |
| 5,356,421 A | 10/1994 | Castro |
| 5,364,365 A | 11/1994 | Wortrich |
| 5,364,372 A | 11/1994 | Danks et al. |
| 5,370,625 A | 12/1994 | Shichman |
| 5,387,197 A | 2/1995 | Smith et al. |
| 5,399,167 A | 3/1995 | Deniega |
| 5,411,515 A | 5/1995 | Haber et al. |
| 5,417,705 A | 5/1995 | Haber et al. |
| 5,431,635 A | 7/1995 | Yoon |
| 5,437,643 A | 8/1995 | Transue |
| 5,441,513 A | 8/1995 | Roth |
| 5,462,532 A | 10/1995 | Gresl |
| 5,474,539 A | 12/1995 | Costa et al. |
| 5,486,190 A | 1/1996 | Green |
| 5,522,833 A | 6/1996 | Stephens et al. |
| 5,527,335 A | 6/1996 | Bolduc et al. |
| 5,538,509 A | 7/1996 | Dunlap et al. |
| 5,549,564 A | 8/1996 | Yoon |
| 5,578,053 A | 11/1996 | Yoon |
| 5,591,190 A | 1/1997 | Yoon |
| 5,626,598 A | 5/1997 | Roth |
| 5,645,556 A | 7/1997 | Yoon |
| 5,645,557 A | 7/1997 | Yoon |
| 5,669,885 A | 9/1997 | Smith |
| 5,674,237 A | 10/1997 | Ott |
| 5,676,156 A | 10/1997 | Yoon |
| 5,697,947 A | 12/1997 | Wolf et al. |
| 5,772,660 A | 6/1998 | Young et al. |
| 5,827,315 A | 10/1998 | Yoon |
| 5,851,216 A | 12/1998 | Allen |
| 5,860,996 A | 1/1999 | Urban et al. |
| 5,868,773 A | 2/1999 | Danks et al. |
| 5,904,699 A | 5/1999 | Schwemberger et al. |
| 5,980,493 A | 11/1999 | Smith et al. |
| 5,984,941 A | 11/1999 | Wilson et al. |
| 6,017,356 A | 1/2000 | Frederick et al. |
| 6,036,711 A | 3/2000 | Mozdzierz et al. |
| 6,063,099 A | 5/2000 | Danks et al. |
| 6,099,544 A | 8/2000 | Wolf et al. |
| 6,238,407 B1 | 5/2001 | Wolf et al. |
| 6,319,266 B1 | 11/2001 | Stellon et al. |
| 2005/0065543 A1 * | 3/2005 | Kahle et al. ............ 606/190 |
| 2005/0119685 A1 | 6/2005 | Smith |
| 2006/0030870 A1 | 2/2006 | Staudner |

FOREIGN PATENT DOCUMENTS

| | | |
|---|---|---|
| EP | 0 617 924 A2 | 2/1994 |
| EP | 0769279 | 4/1997 |
| EP | 1875874 | 1/2008 |
| WO | 94/04206 | 3/1994 |
| WO | 94/22508 | 3/1994 |
| WO | 02/11605 | 2/2002 |
| WO | WO 03/075999 A1 | 9/2003 |

* cited by examiner

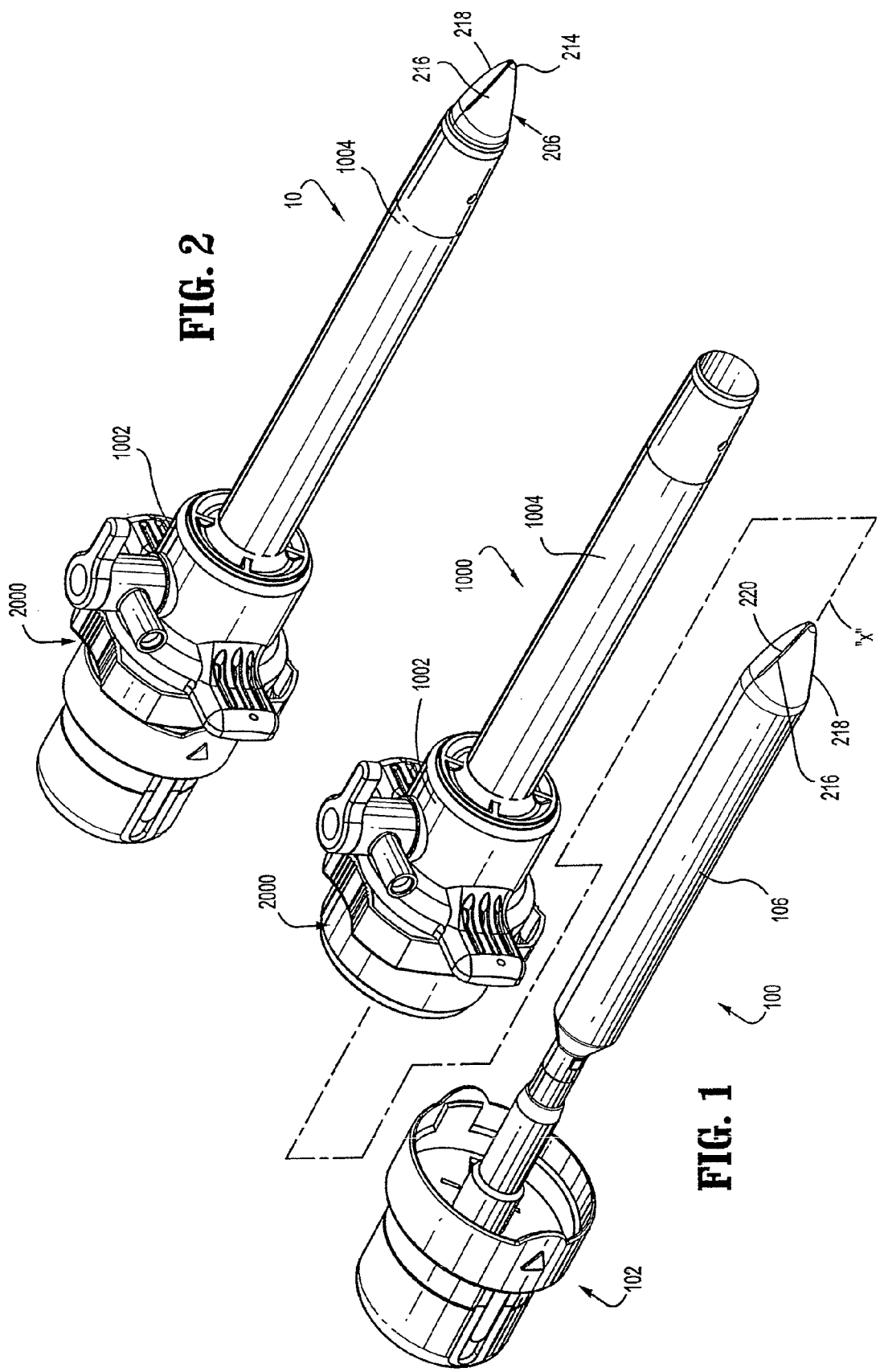

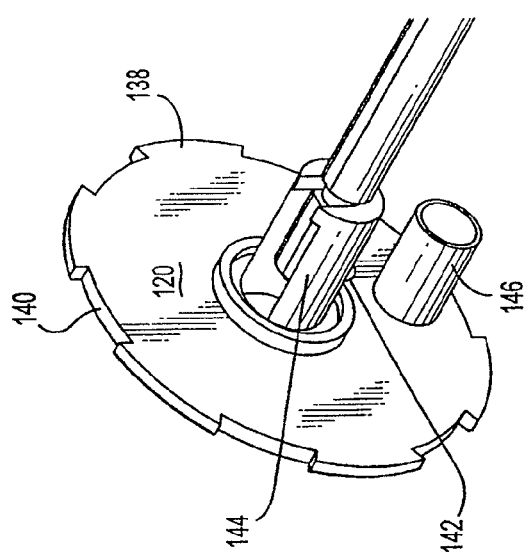
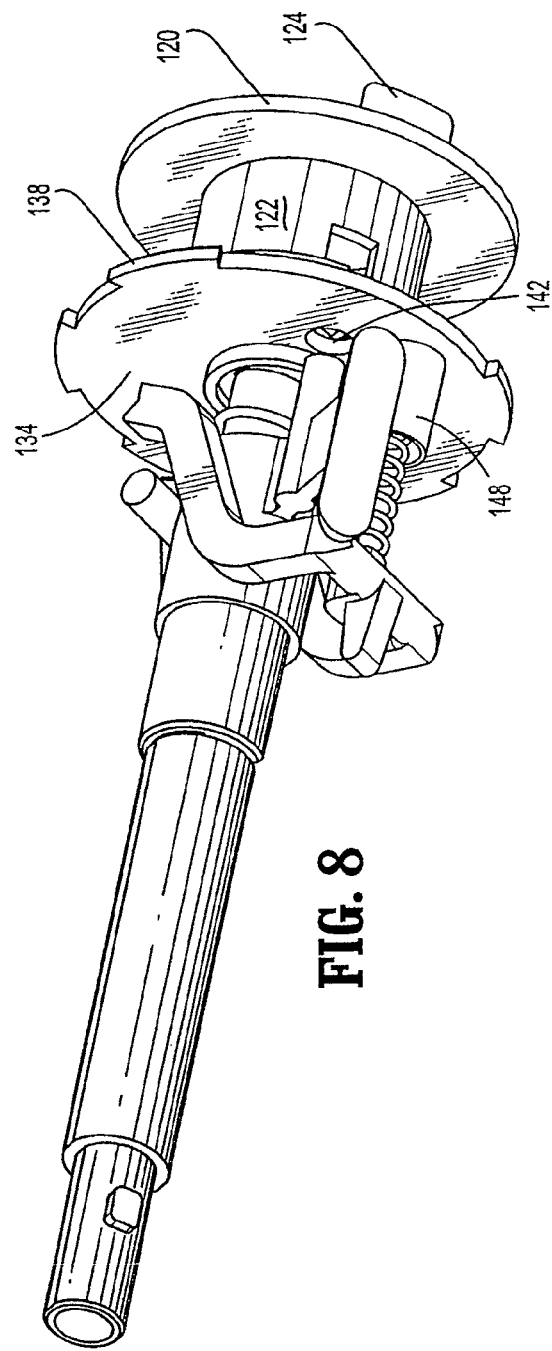
FIG. 9
FIG. 8

TWO-MODE BLADELESS TROCAR ASSEMBLY

CROSS-REFERENCE TO RELATED APPLICATIONS

The present application claims the benefit of and priority to U.S. Provisional Application Ser. No. 60/997,774, filed Oct. 5, 2007, the entire content of which being incorporated herein by reference.

BACKGROUND

1. Technical Field

The present disclosure relates to a bladeless trocar assembly for use in minimally invasive surgical procedures, such as endoscopic or laparoscopic type procedures.

2. Background of the Related Art

Minimally invasive procedures are continually increasing in number and variation. Forming a relatively small diameter temporary pathway to the surgical site is a key feature of most minimally invasive surgical procedures. The most common method of providing such a pathway is by inserting a trocar assembly through the skin. In many procedures, the trocar assembly is inserted into an insufflated body cavity of a patient. In such procedures, the trocar assemblies with seal mechanisms are utilized to provide the necessary pathway to the surgical site while minimizing leakage of insufflation gases.

Trocar assemblies typically include an obturator which is removably inserted through a cannula. The obturator may include a safety shield which protects against unintentional puncturing by the sharpened tip of the obturator. The safety shield includes a mechanism which controls the relative movement and locking of the safety shield. Examples of safety shield mechanisms are disclosed in commonly assigned U.S. Pat. No. 6,319,266 to Stellon et al., and commonly assigned U.S. application Ser. No. 11/171,052, filed Jun. 30, 2005, the entire contents of each disclosure being incorporated herein by reference.

SUMMARY

Accordingly, the present disclosure is directed to further improvements in obturator assemblies. In one preferred embodiment, an obturator assembly for penetrating tissue and being at least partially positionable within a cannula assembly includes an obturator housing, an obturator shaft connected to the obturator housing and defining a longitudinal axis, a bladeless penetrating member adjacent the distal end of the obturator shaft and an obturator shield mounted about the obturator shaft and having a distal shield nose. The obturator shield is adapted for longitudinal movement between an extended position where the bladeless penetration member is substantially enclosed within the shield nose and a retracted position where the bladeless penetrating member is at least partially exposed from the shield nose. A manually manipulative member is mounted to the obturator housing and is adapted for rotational movement about the longitudinal axis and relative to the obturator housing between an initial position corresponding to a first mode of operation where the obturator shield is secured in the extended position and the shield nose is used to penetrate tissue, and a release position corresponding to a second mode of operation operatively releasing the obturator shield to permit the obturator shield to move to the retracted position thereof to expose the bladeless penetrating member for dissecting the tissue. The obturator assembly may further include a latch member disposed within the obturator housing. The preferred latch member is in operative engagement with the obturator shield to secure the obturator shield in the extended position thereof. The latch member is actuable to release the obturator shield when the obturator housing is properly mated with the cannula assembly to thereby permit movement of the obturator shield toward the retracted position provided the manually manipulative member is in the release position. The obturator assembly further includes a release member which is mounted to the obturator housing and operatively coupled with the latch member. The release member is positioned to engage the cannula assembly upon mating of the obturator housing and the cannula assembly to thereby displace the release member and cause actuation of the latch member.

An indicator member may be operatively connected to the obturator shield. The indicator member is adapted for longitudinal movement with the obturator shield to provide visual confirmation to the operator of the positioning of the obturator shield. The manually manipulative member may be in operative engagement with the indicator member when in the initial position of the manually manipulative member to secure the obturator shield in the extended position and is operatively disengaged from the indicator member when in the release position of the manually manipulative member to permit movement of the obturator shield to the retracted position. An indicator collar may be disposed within the obturator housing and mounted to the obturator shield. The indicator collar has the indicator member mounted thereto and is adapted for longitudinal movement with the obturator shield.

Stop means may be associated with the obturator housing for confirming positioning of the manually manipulative member at the initial position and the release position. Alternatively, a control member may be mounted in fixed relation to the obturator housing and operatively associated with the manually manipulative member. One of the control member and the manually manipulative member includes a groove and the other of the control member and the manually manipulative member includes a pin. The pin traverses the groove during rotation of the manually manipulative member between the initial and release position thereof whereby terminating ends of the groove correspond to the initial and release position of the manually manipulative member.

The penetrating member may be a bladeless penetrating member. The bladeless penetrating member may define, from leading to trailing, a cylindrical element having a generally arcuate leading surface and a generally planar dissecting element extending from the cylindrical portion. The obturator shield may be normally biased toward the extended position.

In another embodiment, an obturator assembly for penetrating tissue and being at least partially positionable within a cannula assembly includes an obturator housing defining a longitudinal axis, an obturator shaft connected to the obturator housing, a bladeless penetrating member adjacent the distal end of the obturator shaft and an obturator shield mounted about the bladeless penetrating member and having a shield nose adapted to penetrate tissue. The obturator shield is adapted for longitudinal movement between an extended position where the shield nose substantially encloses the bladeless penetrating member and a retracted position to at least partially expose the bladeless penetrating member. A latch member is disposed within the obturator housing and in operative engagement with the obturator shield to secure the obturator shield in the extended position thereof. The latch member is actuable to release the obturator shield to permit movement of the obturator shield toward the retracted position thereof. A manually manipulative member is mounted to the obturator housing and adapted to be selectively moved by the operator relative to the obturator housing between an initial position corresponding to a first mode of operation securing the obturator shield in the extended position whereby the shield nose is utilized to pass through tissue, and a release position corresponding to a second mode of operation operatively releasing the obturator shield to permit the obturator shield to move to the retracted position thereof provided the latch member is actuated to expose the bladeless penetrating member to permit the penetrating member to dissect the tissue. The manually manipulative member may be adapted for rotational movement relative to the obturator housing to move between the initial position and the release position. A release member may be mounted to the obturator housing and operatively coupled with the latch member. The release member is positioned to engage the cannula assembly upon mating of the obturator housing and the cannula assembly to thereby displace the release member and cause actuation of the latch member.

An indicator member may be operatively connected to the obturator shield. The indicator member is adapted for longitudinal movement with the obturator shield and for providing visual confirmation to the operator of the positioning of the obturator shield. The manually manipulative member is in operative engagement with the indicator member when in the initial position of the manually manipulative member to secure the obturator shield in the extended position, and is operatively disengaged from the indicator member when in the release position of the manually manipulative member to permit movement of the obturator shield to the retracted position provided the latch member is actuated.

In another preferred embodiment, a trocar assembly includes a cannula including a cannula housing and a cannula sleeve extending from the cannula housing and an obturator assembly at least partially positionable within the cannula. The obturator assembly includes an obturator housing, an obturator shaft connected to the obturator housing, a bladeless obturator member connected to the obturator shaft and an obturator shield coaxially mounted about the bladeless obturator member. The obturator shield is adapted for longitudinal movement between a first position substantially enclosing the bladeless obturator member and a second position to at least partially expose the bladeless obturator member. A manually manipulative member is mounted to the obturator housing and is adapted to be selectively moved by the operator relative to the obturator housing between an initial position corresponding to a first mode of operation where a generally blunt leading end of the obturator shield is used to penetrate tissue, and a release position corresponding to a second mode of operation operatively releasing the obturator shield to permit the obturator shield to move to the retracted position thereof to at least partially expose the bladeless obturator member for dissecting the tissue. A latch member is disposed within the obturator housing and in operative engagement with the obturator shield to secure the obturator shield in the extended position thereof. The latch member is actuable to release the obturator shield upon approximating the obturator housing and the cannula housing. The manually manipulative member may be adapted for rotational movement relative to the obturator housing to move between the initial position and the release position.

Methods of use of the obturator assembly are also disclosed.

BRIEF DESCRIPTION OF THE DRAWINGS

Preferred embodiments of the present disclosure are described hereinbelow with references to the drawings, wherein:

FIG. 1 is a perspective view of the trocar assembly in accordance with the present disclosure, illustrating the cannula assembly and the obturator assembly;

FIG. 2 is a perspective view of the trocar assembly illustrating the obturator assembly assembled within the cannula assembly;

FIGS. 7-8 are perspective views of the obturator housing with the housing cover removed;

FIG. 9 is an enlarged perspective view of the control member of the obturator housing;

DETAIL DESCRIPTION OF PREFERRED EMBODIMENTS

Figure 3:
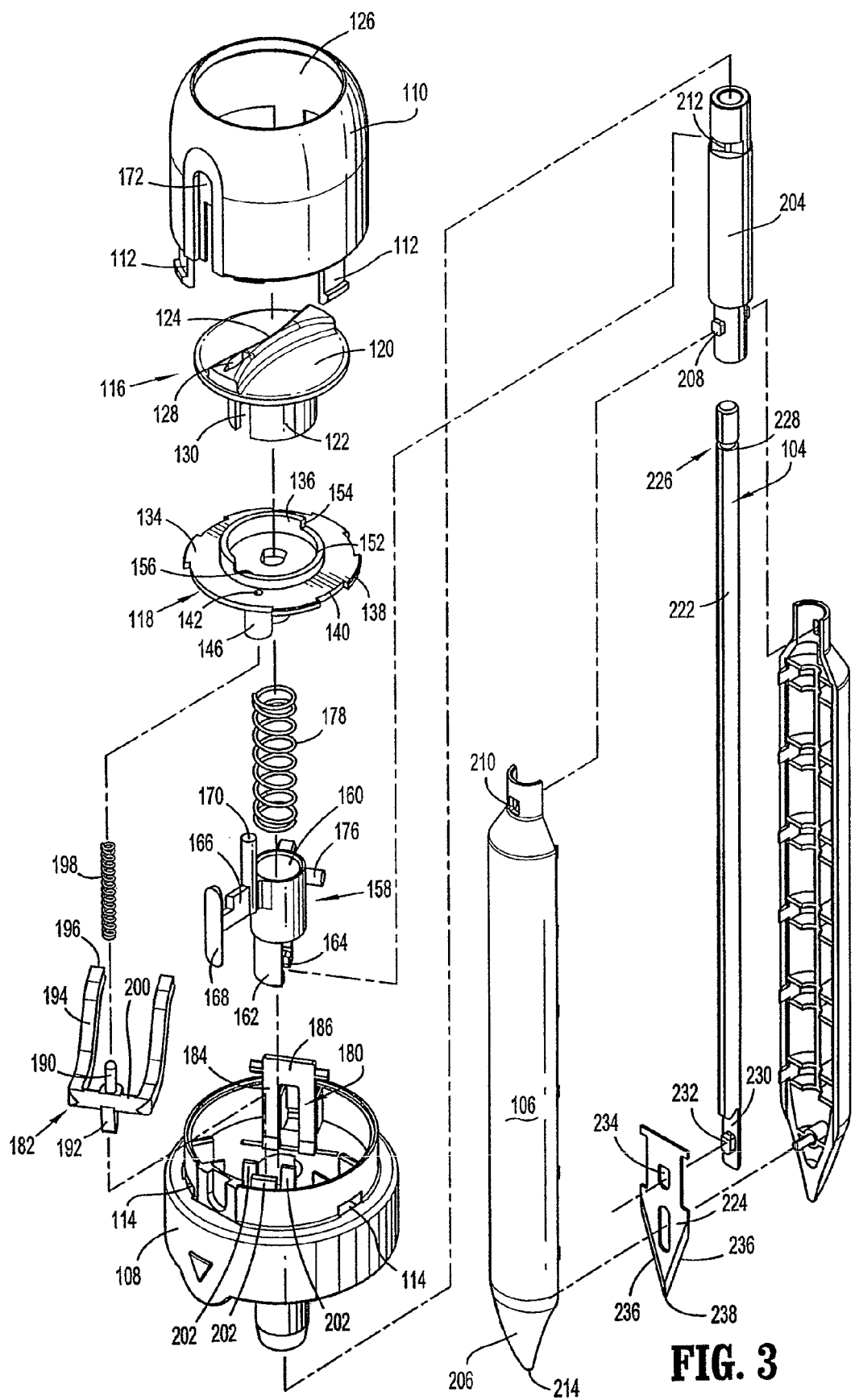
FIG. 3 is a perspective view with parts separated of the obturator assembly.

Referring now in detail to the drawing figures, in which like references numerals identify similar or identical elements, there is illustrated, in FIGS. 1 and 2, a trocar assembly constructed in accordance with a preferred embodiment of the present disclosure, and designated generally by reference numeral 10. Trocar assembly 10 is particularly adapted for use in minimally invasive surgical procedures such as endoscopic or laparoscopic procedures. Generally, trocar assembly 10 includes two principal subassemblies, namely, obturator assembly 100 and cannula assembly 1000.

Cannula assembly 1000 may be any cannula assembly suitable for use in a laparoscopic surgical procedure. In one preferred embodiment, cannula assembly 1000 includes cannula housing 1002 and cannula sleeve 1004 extending from the cannula housing 1002. Either or both cannula housing 1002 and cannula sleeve 1004 may be opaque or transparent in part or in whole and are fabricated from biocompatible metal or polymeric material. Cannula assembly 1000 may include an internal seal such as a duck-bill valve or other zero closure valve adapted to close in the absence of a surgical instrument to prevent passage of insufflation gases through the cannula assembly 1000.

Trocar assembly 10 may also include a seal assembly 2000 which is preferably releasably mounted to cannula housing 1002. Means for releasably connecting seal assembly 2000 to cannula housing 1002 may include a bayonet coupling, threaded connection, latch, friction fit, tongue and groove arrangements, snap-fit, etc. Seal assembly 2000 includes seal housing 2002 and at least one internal seal which is adapted to form a fluid tight seal about an instrument inserted through the seal assembly 2000. One suitable seal may be the fabric seal disclosed in commonly assigned U.S. Pat. No. 6,702,787 to Racenet et al., the entire contents of which are incorporated herein by reference. The seal disclosed in the Racenet '787 patent may be a flat septum seal having a first layer of resilient material and a second fabric layer juxtaposed relative to the first layer. Further details of the seal may be ascertained by reference to the '787 patent. Seal assembly 2000 may or may not be a component of cannula assembly 1000. For example, the seal assembly may be a separate, removable assembly. In the alternative, the seal assembly may comprise an integral part of the cannula assembly 1000 and not be removable.

With reference now to FIG. 3, in conjunction with FIGS. 1-2, obturator assembly 100 includes obturator housing 102, obturator shaft 104 defining obturator axis "x" and extending distally from the housing 102 and obturator shield 106 coaxially mounted about the obturator shaft 104. In general, in a first preferred mode of operation, obturator shield 106 defines a distal shield nose 206 which may be used to enter, penetrate or pass, etc. through tissue through a blunt or dissection entry. Alternatively, in a second mode of operation, obturator shield 106 is permitted to retract in a proximal longitudinal direction to expose the cutting blade disposed at the distal end of the obturator shaft 104. The details of operation and the configuration of shield nose 206 and the cutting blade will be discussed hereinbelow.

Figure 4:
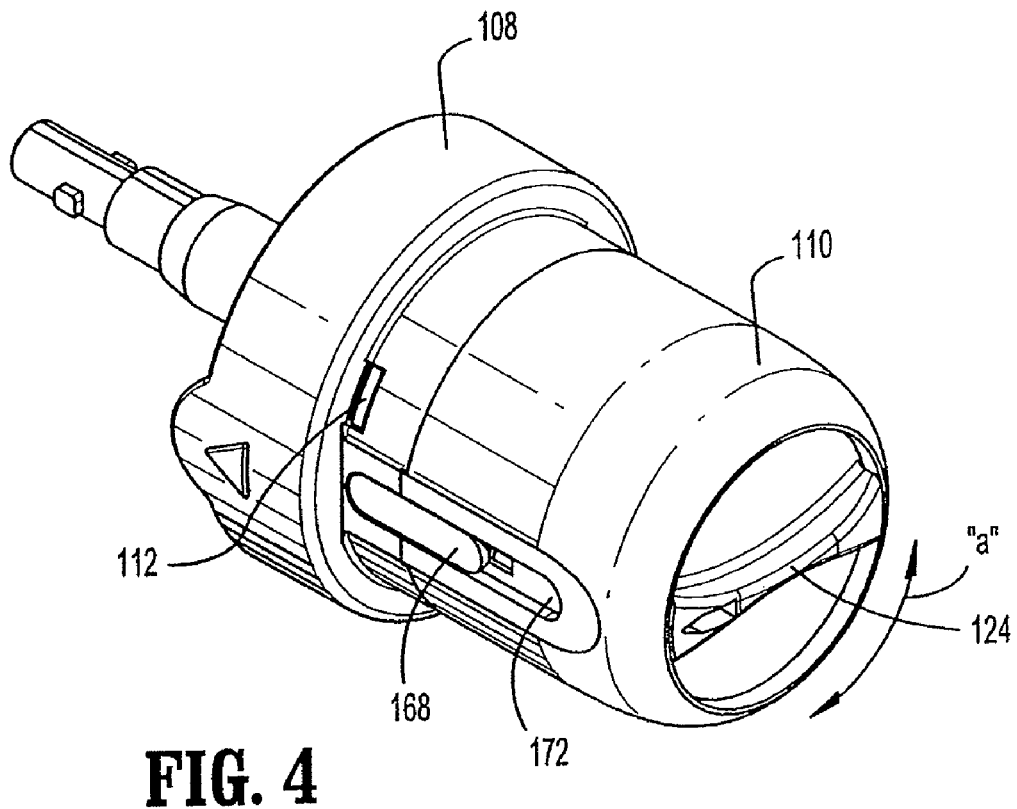
FIG. 4 is a perspective view of the obturator housing of the obturator assembly.
Figure 5:
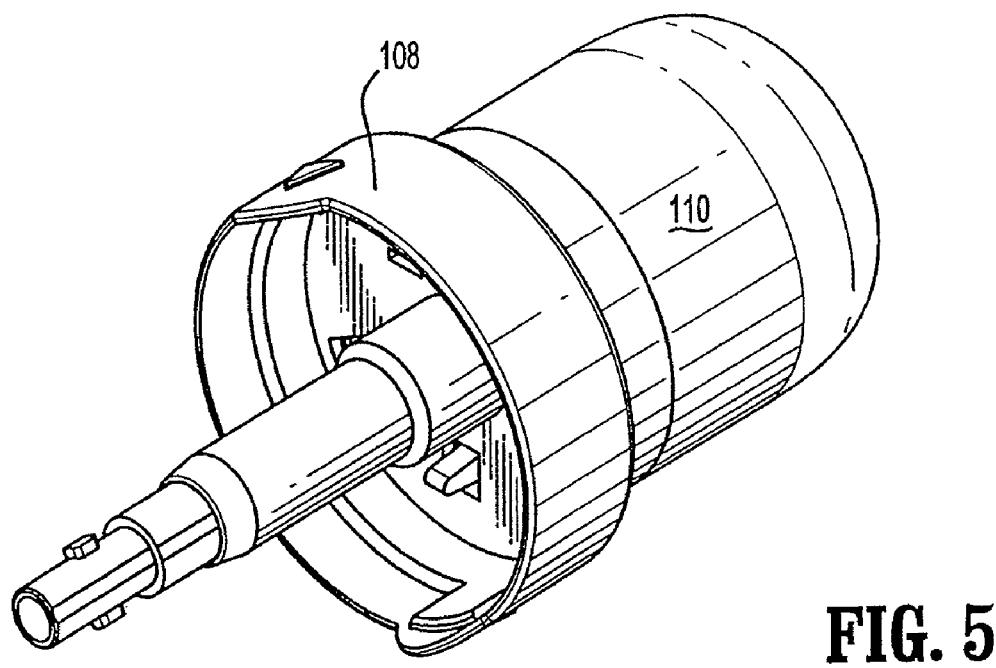
FIG. 5 is a second perspective view of the obturator housing of the obturator assembly.

Referring now to FIGS. 3-5, obturator housing 102 includes housing base 108 and housing cover 110. Once the appropriate components are positioned therewithin (as described below), housing base 108 may be attached to housing cover 110 by engaging mating surfaces, for example, by resilient depending latches 112 of cover 110 interlocking with correspondingly dimensioned latch openings 114 of housing base 108. Preferably, to uniformly connect base 108 and cover 110, at least three corresponding latches 112 and openings 114 are spaced evenly around the circumference of the cover 110 and the base 108, respectively. Preferably, obturator housing 102 is configured and dimensioned to functionally cooperate with cannulas that range in size, e.g., from about 5 mm to about 15 mm in diameter.

Figure 6:
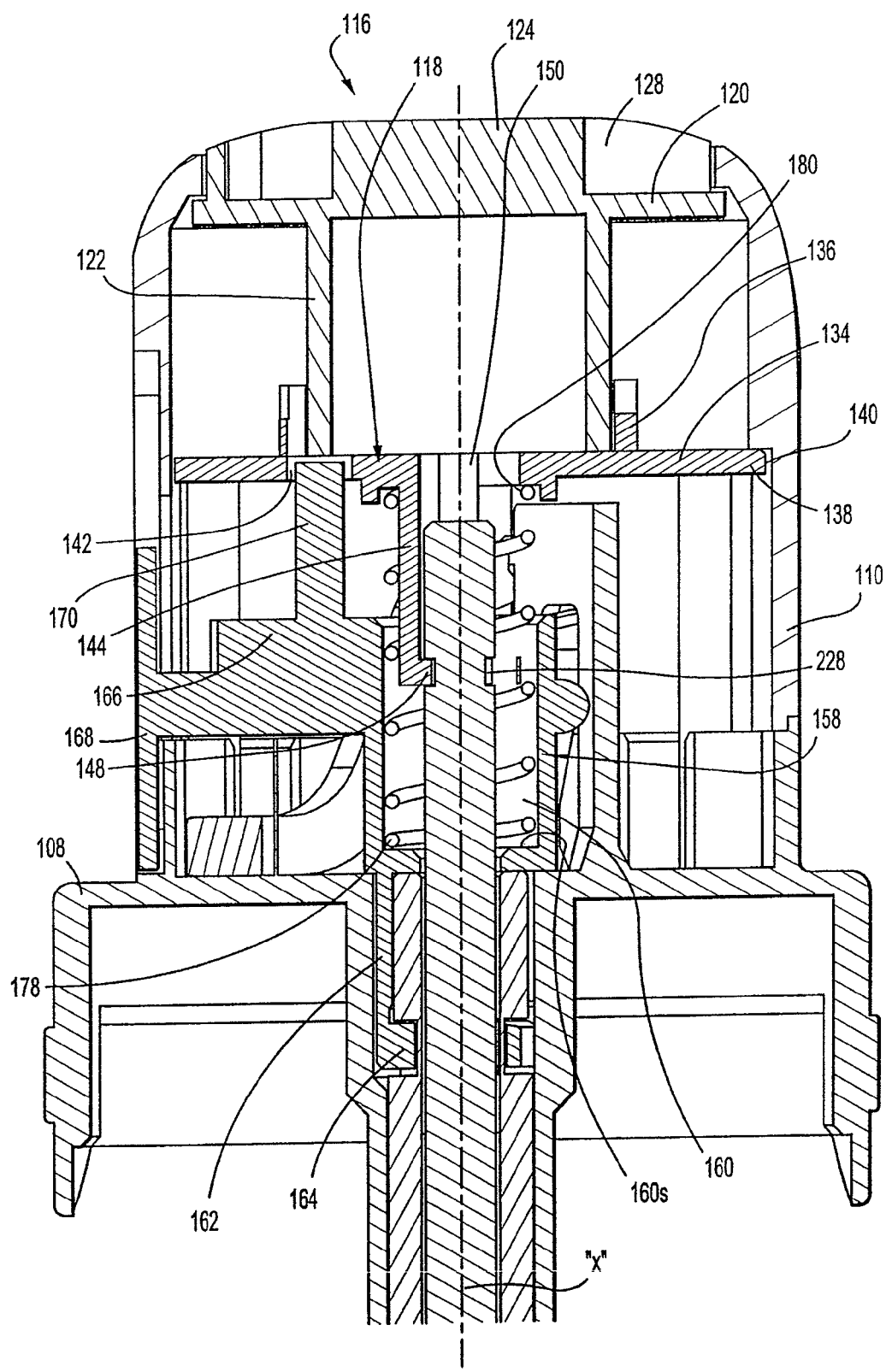
FIG. 6 is a side cross-sectional view of the obturator housing of the obturator assembly illustrating the activator member in an initial position corresponding to a first mode of operation of the obturator assembly.

Referring now to FIGS. 4-7, in conjunction with FIG. 3, obturator housing 102 further includes dial or activator member 116 and control member 118 both of which are housed within the obturator housing 102. Manually manipulative member or activator member 116 defines activator disk 120 and activator collar 122 extending distally from the activator disk 120. Activator disk 120 defines raised tab 124 which is contoured for manual engagement by the fingers of the operator. Raised tab 124 extends beyond opening 126 of housing cover 110. Raised tab 124 further includes indicia in the form of recessed arrow 128 which identifies the status or position of activator member 116. Activator collar 122 includes axial slot 130 and axial rib 132 (FIG. 7) in diametrical opposed relation to the axial slot 130. Activator member 116 is adapted for limited rotational movement as depicted by directional arrow "a" about longitudinal axis "x" between initial and release positions to respectively secure and release obturator shield 106 (FIG. 4). The initial position of activator member 116 corresponds to the first mode of operation of obturator assembly 100 where obturator shield 106 is prevented from retracting and the distal shield nose 206 is used to pass through tissue. FIG. 6 illustrates the initial position of activator member 116. The release position corresponds to the second mode of operation of obturator assembly 100 where obturator shield 106 is permitted to retract and the cutting blade is used to pierce through tissue.

With reference to FIGS. 6-9, in conjunction with FIG. 3, control member 118 is fixed within obturator housing 102. Control member 118 includes control disk 134 and limiting collar 136 extending from the proximal side or face of control disk 134. Control disk 134 includes a plurality of alternating tabs 138 and recesses 140 disposed along the outer periphery of the control disk 134. Tabs 138 are received within corresponding internal recesses 140 (FIG. 6) defined in the inner wall of housing cover 110 to secure control member 118 within obturator housing 102. Control member 118 also includes secondary aperture 142 which is radially or laterally spaced from longitudinal axis "x". Control disk 134 further includes cylindrical shaft mount 144 and spring mount 146 both of which extend from the distal face of the control disk 134. As best depicted in FIG. 6, shaft mount 144 is generally aligned with longitudinal axis "x" and includes bifurcated tabs 148 and central channel 150. Spring mount 146 is laterally or radially spaced from the longitudinal axis "x".

Figure 7:
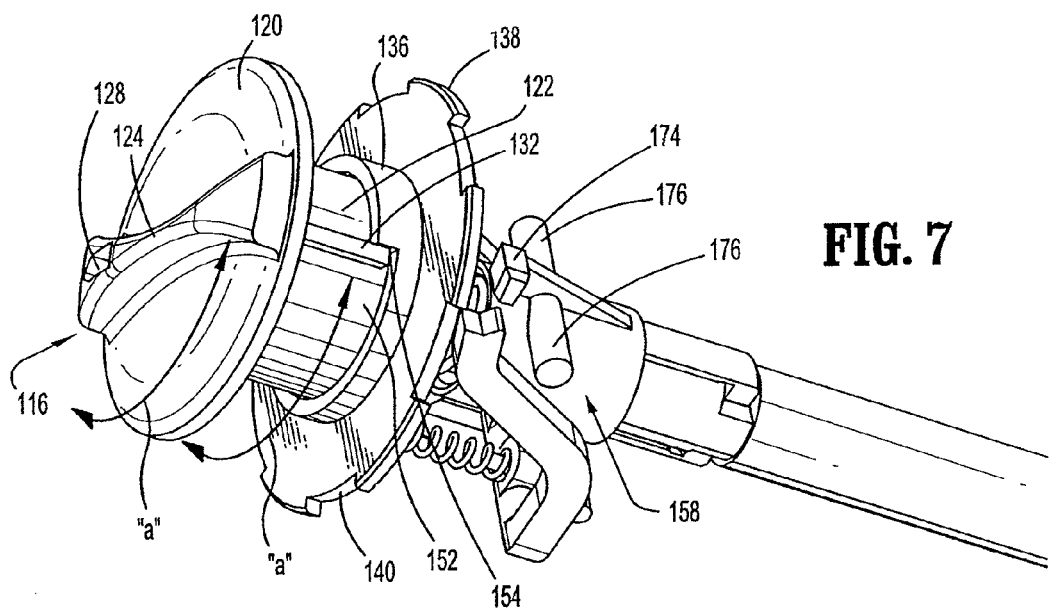

With reference to FIG. 7, limiting collar 136 of control member 118 is dimensioned to receive activator collar 122 of activator member 116 in the assembled condition of the components, and to permit the activator collar 122 to rotate within the limiting collar 136. Limiting collar 136 defines recessed groove 152 which extends about ½ the perimeter of the limiting collar 136. Axial rib 132 of activator member 116 traverses recessed groove 152 of control member 118 during rotation of the activator member 116 between the initial and release positions. As best depicted in FIG. 3, recessed groove 152 defines abutment walls 154, 156 at each end of the recessed groove 152. Abutment walls 154, 156 serve as stop means or stop(s) to ensure and/or confirm placement of activator member 116 in the initial or release position. Specifically, abutment walls 154, 156 serve as a tactile indicator that activator member 116 has been moved to either the initial or release position.

Referring now to FIGS. 3, 6, and 7, obturator housing 100 further includes indicator member or collar 158. In one preferred arrangement, indicator collar 158 defines internal channel 160 and has distal collar extension 162. Collar extension 162 includes inner tabs 164 on its inner surface. Indicator collar 158 further includes transverse arm 166 extending radially outwardly from indicator collar 158 and shield position indicator, such as indicator flag 168. Transverse arm 166 includes axial pin 170 which depends in a proximal direction from the arm 166. Axial pin 170 is in general axial alignment with secondary aperture 142 of control member 118 and traverses the secondary aperture 142 during proximal movement of the indicator collar 158. Indicator flag 168 is visible from the exterior of obturator housing 102 as it extends through groove 172 of housing cover 110 (see FIGS. 3 and 4). Preferably, indicator flag 168 is colored to contrast sharply with the surrounding housing components. For example, indicator flag 168 may be red if the surrounding housing components are white or light colored. As best depicted in FIG. 7, indicator collar 158 further includes collar ledge 174 and a pair of posts 176 formed below the ledge 174 and extending radially outwardly from the ledge 174.

As best depicted in FIG. 6, indicator collar 158 is spring biased in the distal direction by coil spring 178. In particular, coil spring 178 is received within internal channel 160 of indicator collar 158 and engages internal shelf 160s of the indicator collar 158. The proximal end of coil spring 178 is coaxially positioned about spring mount 144 depending from the distal face of control member 118.

Referring now to FIGS. 10-13, in conjunction with FIG. 3, obturator assembly 100 includes a latching mechanism disposed within obturator housing 102 to prevent proximal movement of obturator shield 106 until such time as the obturator assembly 100 is properly mounted to cannula assembly 1000 and the surgeon is prepared to begin trocar entry. Latching mechanism includes latch member 180, and release member such as slider 182. Latch member 180 has two vertical legs 184 connected by web 186. A pair of biasing posts 188 extends outwardly, one for each side of latch member 180. Collar ledge 174 of indicator collar 158 is engaged and secured by web 186 of latch member 180 when in an unactuated position of the latch member 180 as depicted in FIGS. 10-13. In the unactuated position of latch member 180 of indicator collar 158, the indicator collar 158 and thus obturator shield 106 is retained in a first extended position. Latch member 180 is preferably molded as part of housing base 108 in cantilever fashion. However, latch member 180 may be formed as a separate element and secured to base 108 by suitable known techniques.

Figure 11:
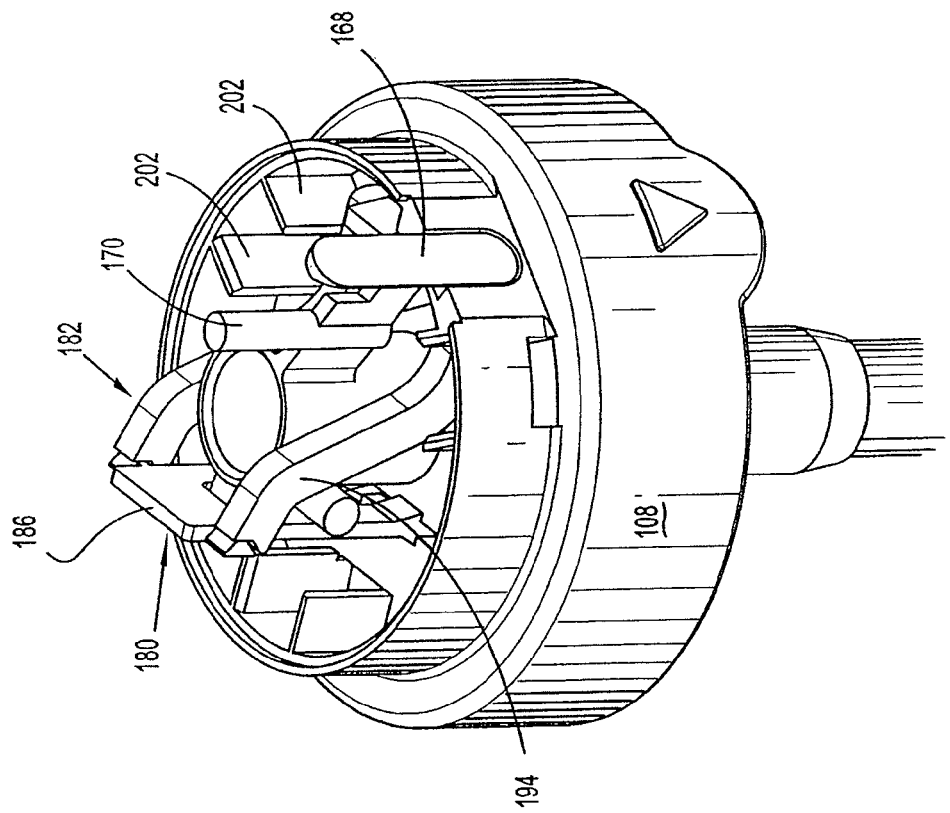
FIGS. 10-11 are additional perspective views of the obturator housing with the housing cover removed.
Figure 10:
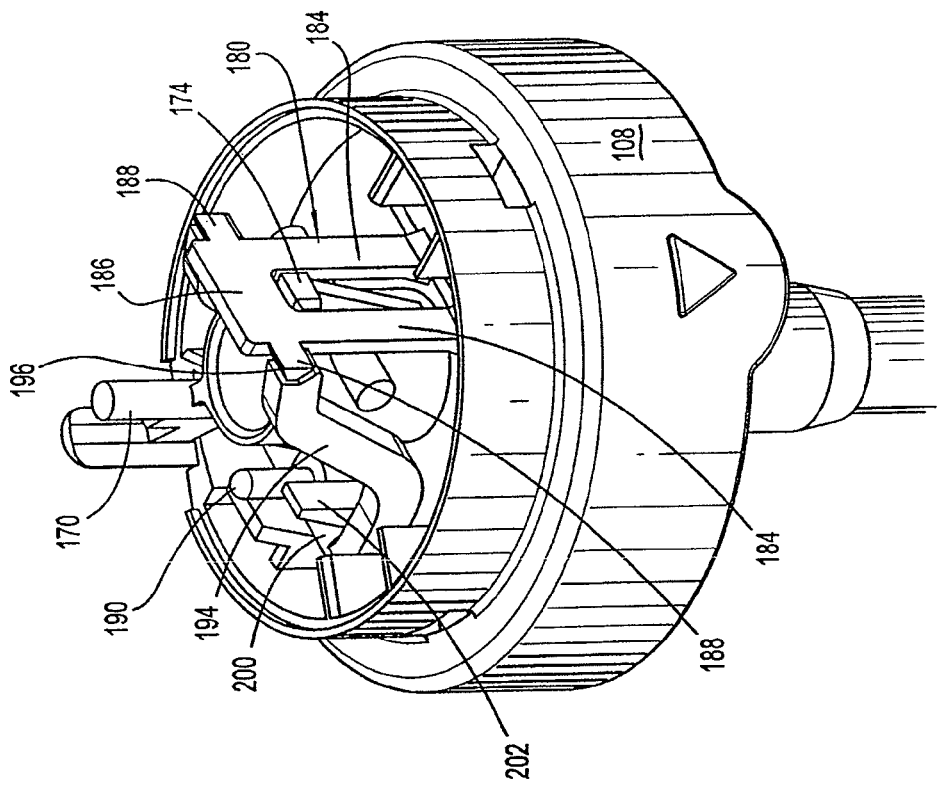

Slider 182 includes slider post 190 disposed at its lower end, arming button 192 extending distally from the distal face of slider 182 and a pair of slider legs 194 which terminate in crooks 196. Crooks 196 defined in slider legs 194 are configured and dimensioned to engage posts 188 of latch member 180, as shown in FIGS. 10 and 11. Slider 182 is distally biased by slider spring 198 which is maintained in axial alignment by slider post 190 of slider 182. The proximal end of slider spring 198 bears against the inner surface of control member 118 and is maintained in position between slider post 190 and spring mount 146 of the control member 118. (See FIGS. 12 and 13). The distal biasing of slider 182 causes arming button 192 to project through opening 108a formed in housing base 108. The lower end or transverse leg 200 of slider 182 resides with mounting posts 202 of housing base 108 (FIG. 3).

Figures 12, 13:
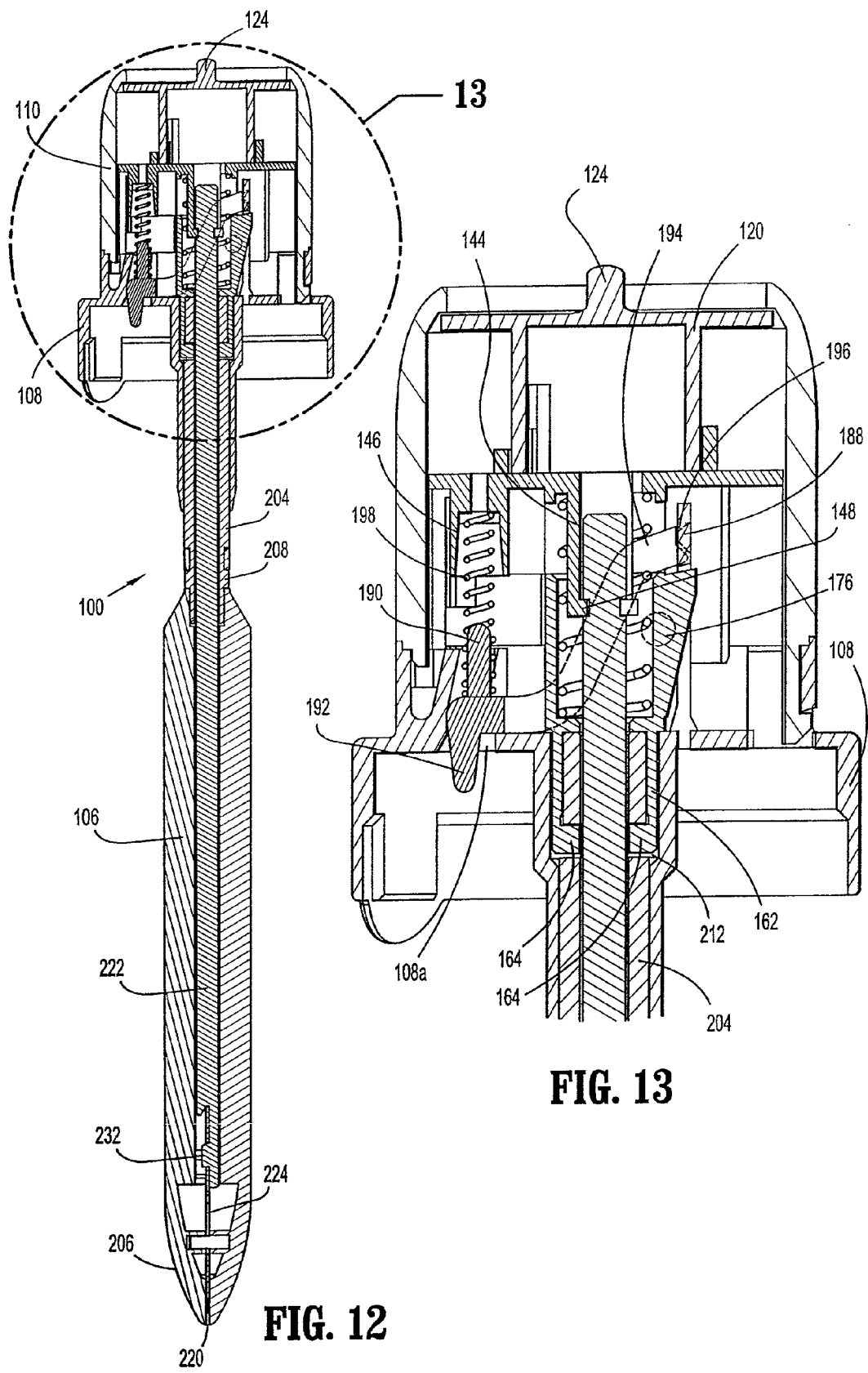
FIG. 12 is a side cross-sectional view of the obturator assembly illustrating the latch member in an unactuated position.
FIG. 13 is an enlarged isolated view of the indicated area of detail of FIG. 12 illustrating the relationship of the components of the latch member in the unactuated position.

Referring now to FIGS. 3 and 12-13, obturator shield 106 has shield linkage 204 operatively connected thereto and along with the obturator shield 106 defines an outer member of obturator assembly 100. In one preferred embodiment, shield linkage 204 is connected to obturator shield 106 through an arrangement including diametrical tabs 208 extending from the distal end of shield linkage 204, which are received within corresponding openings 210 of obturator shield 106 in snap relation therewith. Other means for connecting the components of obturator shield 106 are also envisioned including snap fit arrangements, adhesives, welding tongue and groove arrangements, etc. In other embodiments, obturator shield 106 and shield linkage 204 are a single component. In the assembled condition, shield linkage 204 extends within housing base 108 and is at least partially received within collar extension 162. Shield linkage 204 includes a pair of diametrically opposed outer grooves 212 which receive inner tabs 164 of collar extension 162 to operatively connect shield extension 204 and indicator collar 158. Thus, by virtue of connection of indicator collar 158 with shield linkage 204, obturator shield 106 and shield nose 206 are adapted for reciprocal axial movement along axis "x" and relative to obturator housing 102 and obturator shaft 104 concurrently with corresponding movement of the indicator collar 158.

With reference again to FIGS. 1 and 2, shield nose 206 may be tapered, conical or frusto-conical in configuration, and is adapted to pass through tissue and may be capable of cutting or piercing through tissue. In one preferred embodiment, shield nose 206 has an irregular shaped with rounded tip 214. In particular, shield nose 206 is generally tapered in configuration defining a complex curved arrangement. As best depicted in FIG. 2, in a first profile of shield nose 206, the shield nose 206 includes opposed concave surfaces 216. In a second profile (viewed at a 90° offset), shield nose 206 defines convex surfaces 218. This alternating concave and convex arrangement provides a substantially reduced profile (in cross-section) compared to conventional conically shaped obturators thereby providing an enhanced ability to penetrate or pass through tissue layers. Various radii of curvature are contemplated. Rounded tip 214, by its arcuate configuration, minimizes the potential of undesired or unintended piercing of tissue. Alternatively, it is envisioned that rounded tip 214 may be more pointed to also pierce tissue if desired. This particular configuration of shield nose 206 is disclosed in commonly assigned U.S. Patent Publication No. 2006/0226655, filed Oct. 12, 2006, the contents of which are incorporated in its entirety by reference herein. Shield nose 206 also defines knife slot 220.

With reference to FIGS. 3, 6 and 13, the components of obturator shaft 104 now will be discussed. Obturator shaft 104 includes obturator rod 222 and blade 224 mounted to the obturator rod 222. Obturator rod 222 defines proximal end 226 which passes through opening 160 of indicator collar 158 and is received within shaft mount 144 of control member 118. Proximal end 226 of obturator rod 222 includes circumferential recess 228 which receives bifurcated tabs 148 of shaft mount 144 of control member 118 in snap relation therewith. In this manner, obturator rod 104 is fixed to obturator housing 102.

With reference now to FIG. 12, in conjunction with FIG. 3, the distal end of obturator rod 222 defines obturator knife slot 230 having locking projection 232. Knife blade 224 may be secured within knife slot 230 by reception of locking projection 232 within knife aperture 234. Conventional means including adhesives, cements, etc. are also envisioned. Knife blade 224 is preferably a flat or thin blade and fabricated from stainless steel by a suitable process, e.g., by stamping or metal injection molding and includes opposed cutting edges 236 which extend to penetrating tip 238. Knife blade 224 is accommodated within knife slot 220 of shield nose 206.

Figures 14, 15:
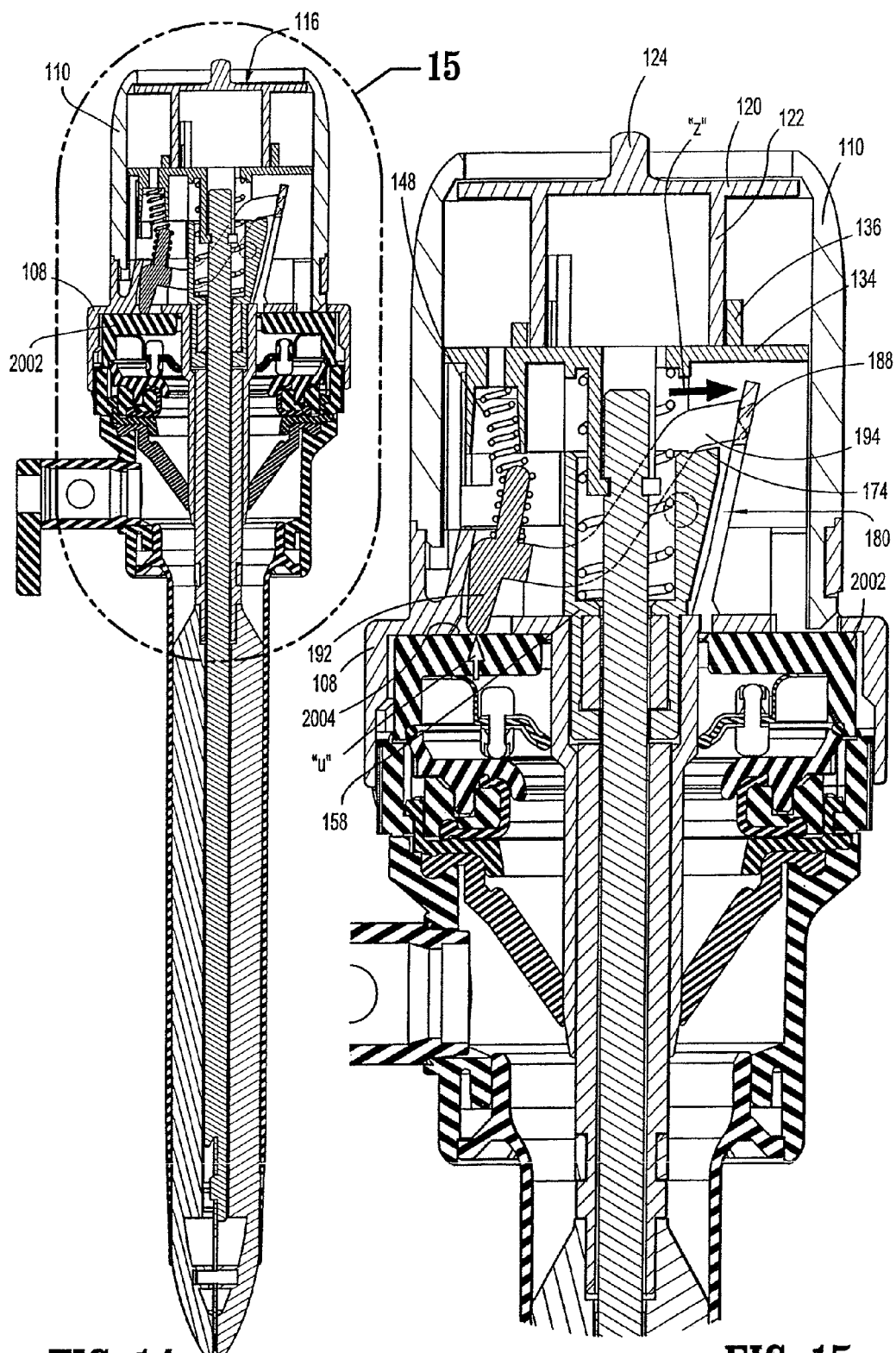
FIG. 14 is a side cross-sectional view of the trocar assembly illustrating the obturator assembly mounted relative to the cannula assembly and the latch member in an actuated position.
FIG. 15 is an enlarged isolated view of the indicated area of detail of FIG. 14 illustrating the relationship of the components of the latch member in the actuated position.

With reference now to FIGS. 14-15, a method of use and operation of trocar assembly 10 will be discussed. Obturator assembly 100 has two modes of operation. In the first mode of operation, obturator shield 106 is locked in its distal position and nose shield 206 is applied against the tissue to penetrate or pass through the tissue through a blunt or dissecting entry. In the second mode, nose shield 206 and obturator shield 106 are permitted to retract to expose knife blade 224 to contact and penetrate the tissue. Activator member 116 controls operation of obturator assembly 100 between the two modes.

Initially, obturator assembly 100 is inserted within cannula assembly 1000 and advanced to where obturator housing 102 is approximated with seal housing 2002 of the seal assembly 2000. Seal assembly 2000 may comprise a separate part or may be a component of cannula assembly 1000. Seal housing 2002 and housing base 108 of obturator housing 102 may be appropriately dimensioned to form a friction fit or may be coupled to each other by conventional means including bayonet coupling, tongue-groove, etc. With obturator housing 102 and seal housing 2002 approximated, arming button 192 of slider 182 engages proximal surface 2004 of seal housing 2002 and is forced upwardly (depicted by directional arrow "u") from the position depicted in FIG. 13 to the position depicted in FIGS. 14-15. During this movement, slider 182 pivots or angulates whereby legs 194 of the slider 182 push latch member 180 in a radial outward direction (depicted by directional arrow "z") such that web portion 186 of latch member 180 is out of axial alignment with ledge 174 of indicator collar 158. In this position, indicator collar 158, obturator shield 106 and shield nose 206 are free to axially move provided activator member 116 is in the second mode of operation. With obturator assembly 100 mated with cannula assembly 2000, the surgeon decides whether a blunt bladeless entry or a piercing blade entry is required to access the surgical site. This decision may be predicated on whether or not an initial entry opening has been made within the tissue, and, if so, thereby requiring a bladeless entry into the tissue corresponding to the first mode of operation of obturator assembly 100. If a bladeless or blunt entry is selected, the surgeon will position activator member 116 in the initial position of FIG. 6. In this position, activator collar 122 is positioned over axial pin 170 of indicator collar 158 and thus prevents proximal retracting movement of the indicator collar 158 and obturator shield 106. Visual confirmation of the positioning of activator collar 122 in the initial position is provided by indicator arrow 128 of raised tab 124. In one preferred embodiment, the initial position of activator collar 122 corresponds to recessed arrow 128 being arranged in diametrical opposed relation to indicator flag 168 as shown in FIG. 6. The surgeon then applies shield nose 206 to the tissue and exerts a distal force on the assembly 10. Shield nose 206 passes through tissue, e.g., by a blunt dissecting action, to access the underlying surgical site, e.g., the abdominal cavity. Obturator assembly 100 may be removed from cannula assembly 1000 and surgery may be performed with instruments introduced within cannula assembly 1000.

Figure 16:
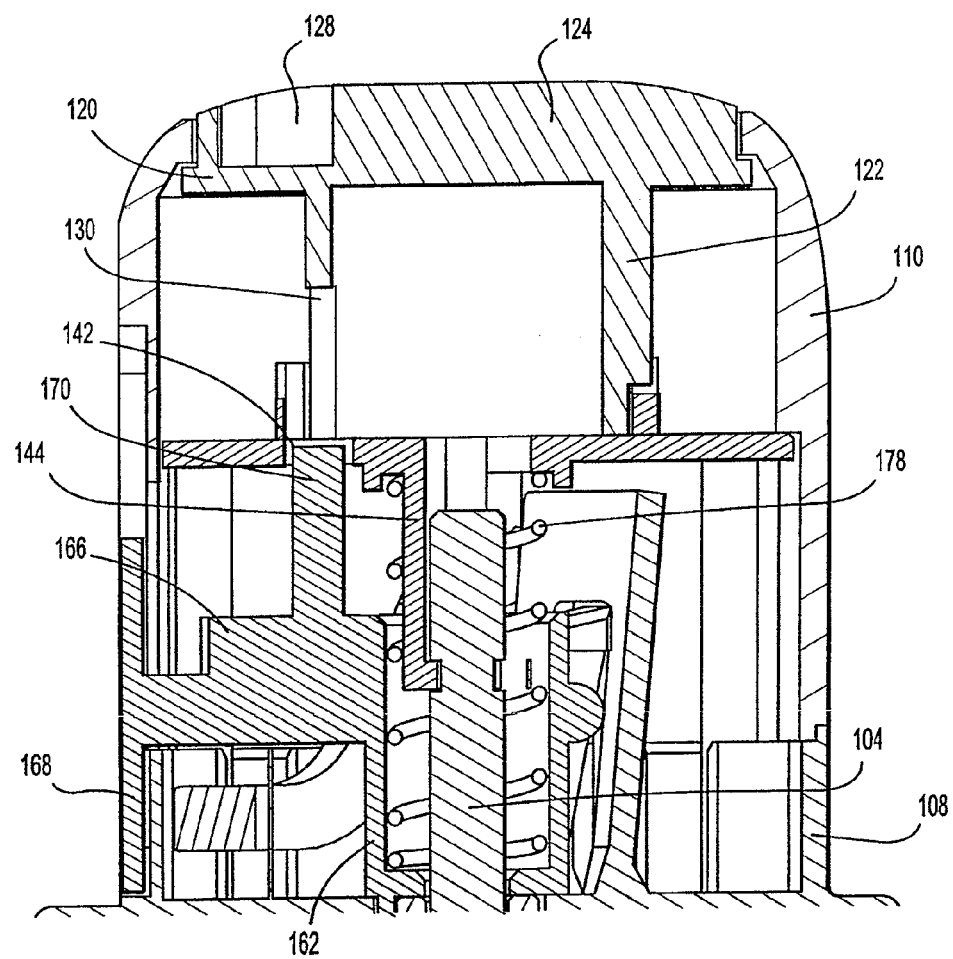
FIG. 16 is a side cross-sectional view of the obturator housing illustrating the activator member in a release position corresponding to a second mode of operation of the obturator assembly.

If a bladed entry is required corresponding to the second mode of operation, activator member 116 is selectively moved from the initial position of FIG. 6 to the release position of FIG. 16 by rotating the activator member 116 about longitudinal axis "x" such that recessed arrow 128 of the activator member 116 is aligned with indicator flag 168 thereby providing visual confirmation of the positioning of activator member 116. Engagement of axial rib 122 of activator member 116 with wall 156 (FIG. 3) of control member 118 also provides tactile confirmation of the positioning of activator member 116 in the release position. In the release position, axial slot 130 of activator collar 122 is in general alignment with axial pin 170 of indicator collar 158.

Figures 17, 18:
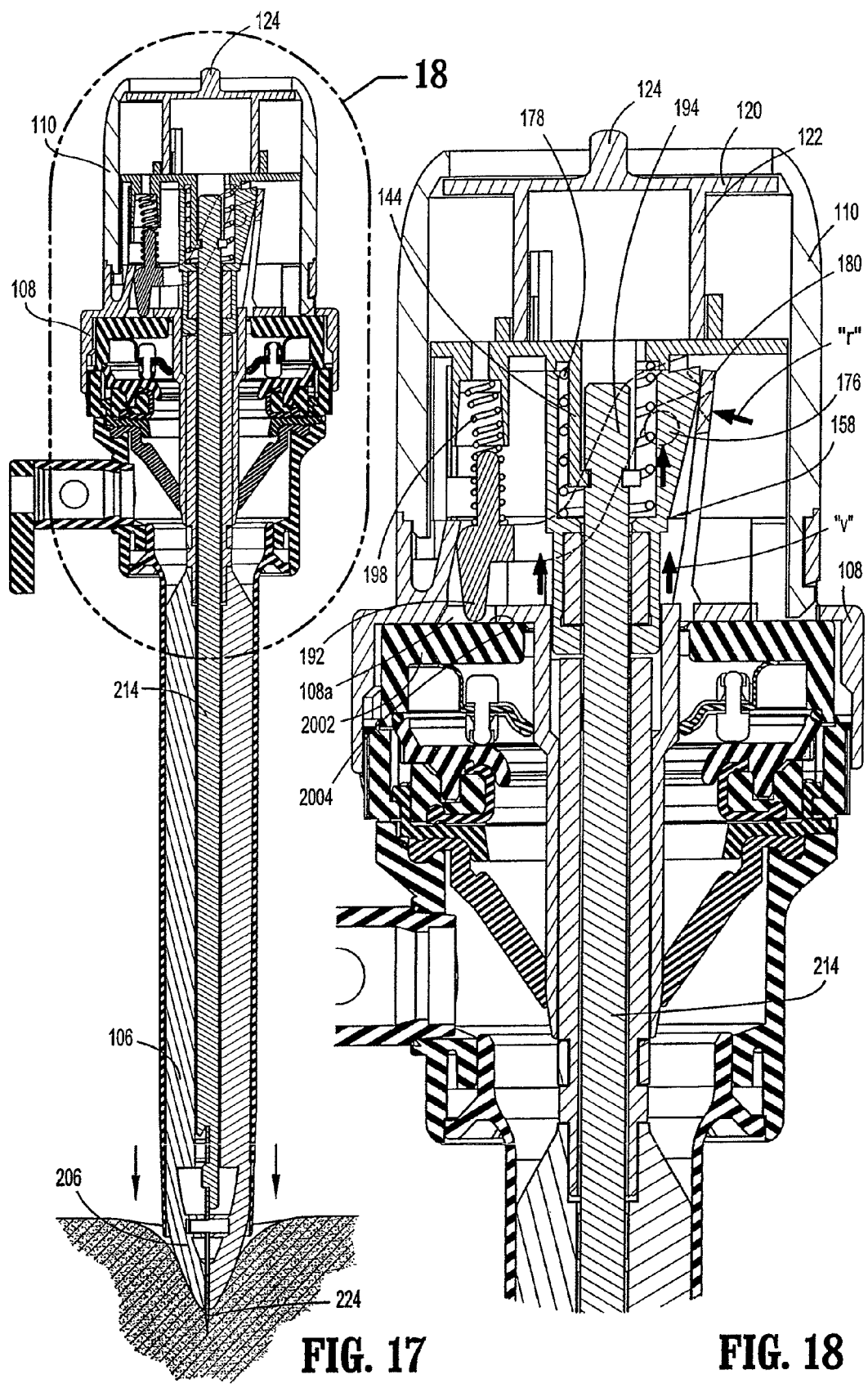
FIG. 17 is a side cross-sectional view similar to the view of FIG. 14 illustrating the obturator shield of the obturator assembly in a retracted position to expose the obturator blade.
FIG. 18 is an enlarged isolated view of the indicated area of detail of FIG. 17.
Figure 19:
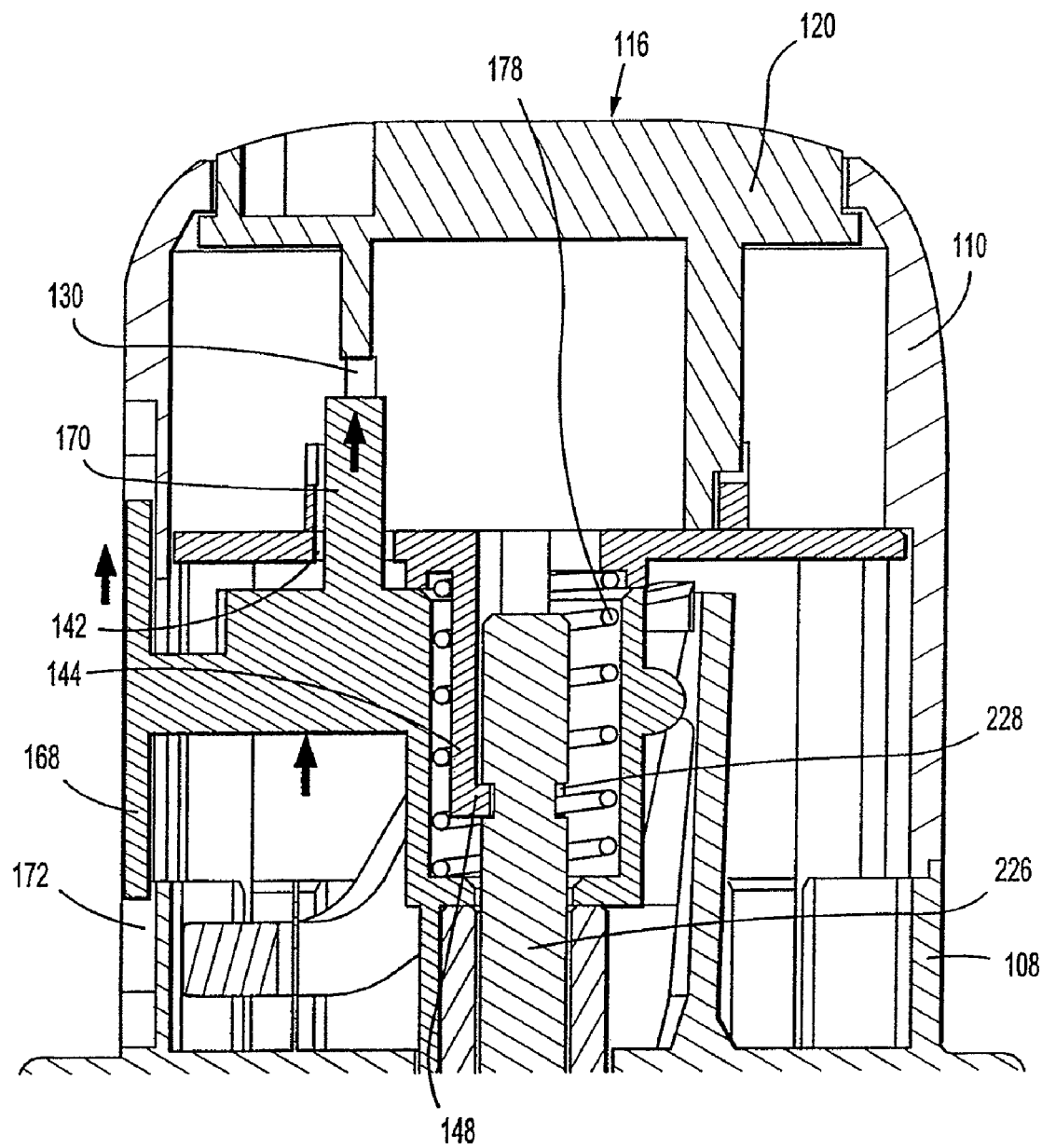
FIG. 19 is a side cross-sectional view illustrating proximal movement of the indicator collar during movement of the obturator shield to the retracted position.

With reference now to FIGS. 17-19, the surgeon begins to insert trocar assembly 10 through the body wall of the patient. Shield nose 206 contacts the tissue "t" and is driven upwardly to cause the shield nose 206, obturator shield 106, and indicator collar 158 to move proximally (depicted by directional arrow "v") against the bias of coil spring 178. As discussed hereinabove, obturator assembly 100 must be properly mated with seal assembly 2000 such that the latching mechanism is activated to permit retraction of obturator shield 106. During the proximal movement of indicator collar 158, axial pin 170 of the indicator collar 158 traverses secondary aperture 142 of control member 118 and traverses axial slot 130 of activator member 116. (FIG. 19) Such movement exposes obturator blade 224 to incise the tissue. This armed condition of obturator assembly 100 is visually verified by the proximal location of indicator flag 168 of indicator collar 158. In addition, proximal movement of indicator collar 158 causes posts 176 of the indicator collar 158 to ride along outer surfaces 194a of legs 194 of slider 182 to thereby move the slider 182 at least radially inwardly and upwardly (as shown by the directional arrows "r" and "v", respectively) in a general aligned position relative to the obturator axis "x" and disengaged from latch member 180. (i.e., crooks 196 of slider legs 194 disengage posts 188 of latch member 180). With obturator blade 224 exposed, the surgeon may apply a distally-directed force to obturator assembly 100 to cause penetration through the tissue.

Once knife blade 224 and shield nose 206 pass through the body wall of the patient, indicator collar 158, obturator shield 106 and the shield nose 206 move distally under the influence of coil spring 178 whereby the shield nose 206 covers blade 224 as shown in FIG. 14. The obturator assembly 100 may be removed from cannula assembly 1000 and surgery is performed with instruments inserted through cannula assembly 1000. It is noted that upon removal of obturator assembly 100, ledge 174 of indicator collar 158 moves into engagement with web portion 186 of latch member 180. Concurrently with this movement, slider 182, which is aligned relative to axis "x" as discussed hereinabove, is driven distally under the influence of coil spring 198. In the respective positions of indicator collar 158 and slider 182 depicted in FIG. 13, collar ledge 174 of indicator collar 158 securely engages web 186 of latch member 180 to secure shield nose 206 in its extended position. This feature ensures that the removed obturator assembly 100 will not be armed.

Except where noted otherwise, the materials utilized in the components of the presently disclosed trocar assembly generally include materials such as, for example, ABS, polycarbonate, stainless steel, titanium and any other suitable biocompatible metals and/or polymeric materials. A preferred ABS material is CYCOLAC which is available from General Electric. A preferred polycarbonate material is also available from General Electric under the trademark LEXAN. An alternative polycarbonate material which may be utilized is CALIBRE polycarbonate available from Dow Chemical Company. The polycarbonate materials may be partially glass filled for added strength.

Figure 20:
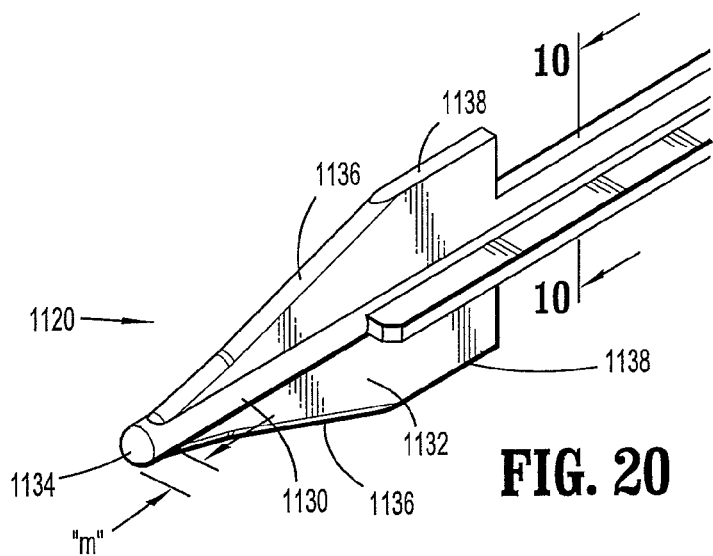
FIG. 20 is a partial perspective view of a bladeless penetrating member of the obturator member, in accordance with an example embodiment of the present invention.

While the various embodiments set forth above illustrate the obturator having a penetrating member that includes sharp blades for incising tissue, the present invention may also include an arrangement in which the penetrating member includes one or more blunt surfaces for dissecting tissue. In such an arrangement, the obturator may be employed in each of its two or more modes of operation without blades, e.g., providing two or more different bladeless arrangements. For example, FIG. 20 is a perspective view of a penetrating member of the obturator member, in accordance with an example embodiment of the present invention. As depicted in FIG. 20, penetrating member 1120 includes, from distal to proximal, cylindrical element 1130 and planar dissecting element 1132 extending contiguously from the cylindrical element 1130. Cylindrical element 1130 defines an arcuate or rounded leading surface 1134 which is atraumatic to tissue and extends a predetermined distance "m" beyond planar dissecting element 1132. This consequent narrow profile provided by cylindrical element 1130 permits initial insertion within tissue and facilitates, e.g., dissection or advancement, within the tissue without an incising action. Cylindrical element 1130 may extend through planar dissecting element 1132 to the obturator rod. Planar dissecting element 1132 defines a triangular arrangement having oblique side surfaces 1136 leading to parallel end surfaces 1138. Side surfaces 1136 may be arcuate or rounded as shown to be atraumatic to tissue. End surfaces 1138 may be blunt.

Figure 21:
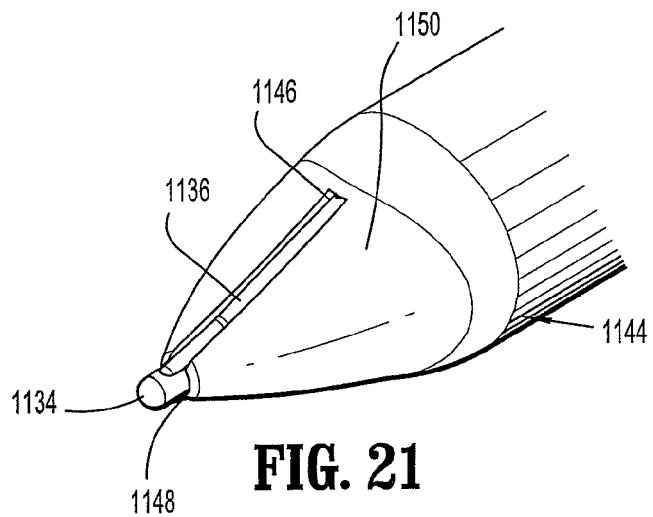
FIG. 21 is a perspective view of a distal end of the obturator assembly with the penetrating member being in an unarmed position, in accordance with the embodiment of FIG. 20.
Figure 22:
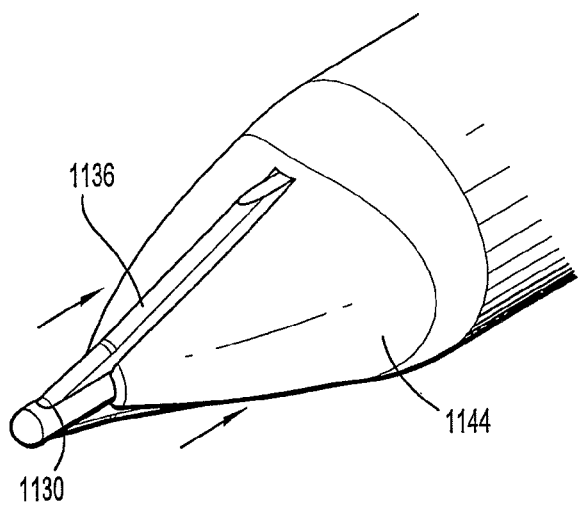
FIG. 22 is a perspective view of a distal end of the obturator assembly with the penetrating member being in an unarmed position, in accordance with the embodiment of FIG. 20.

With reference to FIG. 21, shield nose 1144 is positioned about penetrating member 1120 of the obturator member. Shield nose 1144 defines a central slot 1146 for reception of penetrating member 1120. Shield nose 1144 further defines a central aperture 1148 communicating with central slot 1146 to permit passage of cylindrical element 1130 of penetrating member 1120. Shield nose 1144 moves relative to penetrating member 1120 during longitudinal movement of protective shield 1106. As depicted in FIG. 21, in the initial or unarmed condition, shield nose 1144 is positioned relative to penetrating member 1120 whereby cylindrical portion 1130 of the penetrating member 1120 at least partially extends beyond the shield nose 1144. In addition, side surfaces 1136 of planar dissecting element 1132 also may extend beyond shield nose 1144, i.e., protrude outwardly from central slot 1146. Shield nose 1144 may be generally conical in configuration. Alternatively, shield nose 1144 may also have a slight inward contour 1150 along opposed peripheral portions. Various other configurations are also envisioned. FIG. 22 illustrates the armed condition of penetrating member 1120. In this position, penetrating member 1120 is used, by the surgeon applying a distally-directed force to obturator assembly 100, to penetrate, dissect or pierce through the tissue. Other features of this embodiment, e.g., those that are proximal of shield nose 1144, may be similar to features described hereinabove.

A method of use and operation of the embodiment of trocar assembly 10, as illustrated in FIGS. 20-22 will be discussed. Obturator assembly 100 has two modes of operation. In the first mode of operation, obturator shield 106 is locked in its distal position and shield nose 1144 is applied against the tissue to penetrate or pass through the tissue through a blunt or dissecting entry. In the second mode, shield nose 1144 and obturator shield 106 are permitted to retract to expose portions of the penetrating member 1120, e.g., side surfaces 1136, to contact and penetrate the tissue in a different type of dissecting fashion. Activator member 116 controls operation of obturator assembly 100 between the two modes.

Initially, obturator assembly 100 is inserted within cannula assembly 1000 and advanced to where obturator housing 102 is approximated with seal housing 2002 of the seal assembly 2000. Seal assembly 2000 may comprise a separate part or may be a component of cannula assembly 1000. Seal housing 2002 and housing base 108 of obturator housing 102 may be appropriately dimensioned to form a friction fit or may be coupled to each other by conventional means including bayonet coupling, tongue-groove, etc. With obturator housing 102 and seal housing 2002 approximated, arming button 192 of slider 182 engages proximal surface 2004 of seal housing 2002 and is forced upwardly (depicted by directional arrow "u") from the position depicted in FIG. 13 to the position depicted in FIGS. 14-15. During this movement, slider 182 pivots or angulates whereby legs 194 of the slider 182 push latch member 180 in a radial outward direction (depicted by directional arrow "z") such that web portion 186 of latch member 180 is out of axial alignment with ledge 174 of indicator collar 158. In this position, indicator collar 158, obturator shield 106 and shield nose 1144 are free to axially move provided activator member 116 is in the second mode of operation. With obturator assembly 100 mated with cannula assembly 2000, the surgeon decides which type of blunt bladeless entry is desired to access the surgical site. This decision may be predicated on whether or not an initial entry opening has been made within the tissue, and, if so, thereby requiring a specific type of bladeless entry into the tissue corresponding to the first mode of operation of obturator assembly 100. If a first type of bladeless or blunt entry is selected, the surgeon will position activator member 116 in the initial position of FIG. 6. In this position, activator collar 122 is positioned over axial pin 170 of indicator collar 158 and thus prevents proximal retracting movement of the indicator collar 158 and obturator shield 106. Visual confirmation of the positioning of activator collar 122 in the initial position is provided by indicator arrow 128 of raised tab 124. In one preferred embodiment, the initial position of activator collar 122 corresponds to recessed arrow 128 being arranged in diametrical opposed relation to indicator flag 168 as shown in FIG. 6. The surgeon then applies shield nose 1144 to the tissue and exerts a distal force on the assembly 10. Shield nose 1144 passes through tissue, e.g., by a blunt dissecting action, to access the underlying surgical site, e.g., the abdominal cavity. Obturator assembly 100 may be removed from cannula assembly 1000 and surgery may be performed with instruments introduced within cannula assembly 1000.

If a different type of bladeless entry is required corresponding to the second mode of operation, activator member 116 is selectively moved from the initial position of FIG. 6 to the release position of FIG. 16 by rotating the activator member 116 about longitudinal axis "x" such that recessed arrow 128 of the activator member 116 is aligned with indicator flag 168 thereby providing visual confirmation of the positioning of activator member 116. Engagement of axial rib 122 of activator member 116 with wall 156 (FIG. 3) of control member 118 also provides tactile confirmation of the positioning of activator member 116 in the release position. In the release position, axial slot 130 of activator collar 122 is in general alignment with axial pin 170 of indicator collar 158.

The surgeon begins to insert trocar assembly 10 through the body wall of the patient. Shield nose 1144 contacts the tissue "t" and is driven upwardly to cause the shield nose 1144, obturator shield 106, and indicator collar 158 to move proximally (depicted by directional arrow "v") against the bias of coil spring 178. As discussed hereinabove, obturator assembly 100 may be properly mated with seal assembly 2000 such that the latching mechanism is activated to permit retraction of obturator shield 106. During the proximal movement of indicator collar 158, axial pin 170 of the indicator collar 158 traverses secondary aperture 142 of control member 118 and traverses axial slot 130 of activator member 116. (FIG. 19) Such movement exposes portions of the penetrating member 1120, e.g., side surfaces 1136, to dissect the tissue. This armed condition of obturator assembly 100 is visually verified by the proximal location of indicator flag 168 of indicator collar 158. In addition, proximal movement of indicator collar 158 causes posts 176 of the indicator collar 158 to ride along outer surfaces 194a of legs 194 of slider 182 to thereby move the slider 182 at least radially inwardly and upwardly (as shown by the directional arrows "r" and "v", respectively) in a general aligned position relative to the obturator axis "x" and disengaged from latch member 180 (i.e., crooks 196 of slider legs 194 disengage posts 188 of latch member 180). With portions of the penetrating member 1120, e.g., side surfaces 1136, exposed, the surgeon may apply a distally-directed force to obturator assembly 100 to cause penetration through the tissue.

Once portions of the penetrating member 1120, e.g., side surfaces 1136, and shield nose 1144 pass through the body wall of the patient, indicator collar 158, obturator shield 106 and the shield nose 1144 move distally under the influence of coil spring 178 whereby the shield nose 1144 moves relative to the, e.g., side surfaces 1136, to the position shown in FIG. 21. The obturator assembly 100 may be removed from cannula assembly 1000 and surgery is performed with instruments inserted through cannula assembly 1000. It is noted that upon removal of obturator assembly 100, ledge 174 of indicator collar 158 moves into engagement with web portion 186 of latch member 180. Concurrently with this movement, slider 182, which is aligned relative to axis "x" as discussed hereinabove, is driven distally under the influence of coil spring 198. In the respective positions of indicator collar 158 and slider 182 depicted in FIG. 13, collar ledge 174 of indicator collar 158 securely engages web 186 of latch member 180 to secure shield nose 1144 in its extended position. This feature ensures that the removed obturator assembly 100 will not be armed.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An obturator assembly for penetrating tissue and being at least partially positionable within a cannula assembly, which comprises:
    an obturator housing;
    an obturator shaft connected to the obturator housing and defining a longitudinal axis, and proximal and distal ends;
    a bladeless penetrating member mounted to the distal end of the obturator shaft;
    an obturator shield mounted about the obturator shaft and having a distal shield nose, the obturator shield being adapted for longitudinal movement relative to the obturator housing between an extended position where the bladeless penetrating member is substantially enclosed within the shield nose and a retracted position where the bladeless penetrating member is at least partially exposed from the shield nose;
    an indicator member operatively connected to the obturator shield, the indicator member being adapted for longitudinal movement with the obturator shield and for providing visual confirmation to the operator of the positioning of the obturator shield; and
    a manually manipulative member mounted to the obturator housing and adapted for rotational movement about the longitudinal axis and relative to the obturator housing between an initial position corresponding to a first mode of operation where the obturator shield is secured in the extended position and the shield nose is usable to penetrate tissue, and a release position corresponding to a second mode of operation operatively releasing the obturator shield to permit the obturator shield to move to the retracted position thereof to expose the bladeless penetrating member for dissecting the tissue, the manually manipulative member being in operative engagement with the indicator member when in the initial position of the manually manipulative member to secure the obturator shield in the extended position and being operatively disengaged from the indicator member when in the release position of the manually manipulative member to permit movement of the obturator shield to the retracted position.

2. The obturator assembly according to claim 1 wherein the bladeless penetrating member defines, from leading to trailing, a cylindrical element having a generally arcuate leading surface and a generally planar dissecting element extending from the cylindrical portion.

3. The obturator assembly according to claim 1 wherein the obturator shield is normally biased toward the extended position.

4. The obturator assembly according to claim 3, wherein the obturator shield is dimensioned and adapted to longitudinally move toward the retracted position when the manually manipulative member is in the release position corresponding to the second mode of operation upon engagement of the shield nose with tissue, and is further adapted to return toward the extended position upon passage of the shield nose through tissue and when the manually manipulative member is in the release position corresponding to the second mode of operation.

5. The obturator assembly according to claim 1 including an indicator collar disposed within the obturator housing and mounted to the obturator shield, the indicator collar having the indicator member mounted thereto and being adapted for longitudinal movement with the obturator shield.

6. The obturator assembly according to claim 1 including stop means associated with the obturator housing for confirming positioning of the manually manipulative member at the initial position and the release position.

7. The obturator assembly according to claim 1 further including a latch member disposed within the obturator housing, the latch member in operative engagement with the obturator shield to secure the obturator shield in the extended position thereof, the latch member being actuatable to release the obturator shield to thereby permit movement of the obturator shield toward the retracted position provided the manually manipulative member is in the release position thereof.

8. The obturator assembly according to claim 7 further comprising a release member mounted to the obturator housing and operatively coupled with the latch member, the release member positioned to engage the cannula assembly upon mating of the obturator housing and the cannula assembly to thereby displace the release member and cause actuation of the latch member.

9. The obturator assembly according to claim 1 wherein the obturator shield is adapted for longitudinal movement relative to the bladeless penetrating member between the extended position and the retracted position.

10. The obturator assembly according to claim 1 wherein the manually manipulative member is fixed from longitudinal movement relative to the obturator housing.

11. The obturator assembly according to claim 1 wherein the obturator shaft is secured to the obturator housing and incapable of longitudinal movement relative to the obturator housing.

12. The obturator assembly according to claim 1 wherein the obturator shield is dimensioned and adapted to move repeatedly between the extended position and the retracted position when the manually manipulative member is in the release position corresponding to the second mode of operation.

13. An obturator assembly for penetrating tissue and being at least partially positionable within a cannula assembly, which comprises:
    an obturator housing;

an obturator shaft connected to the obturator housing and defining a longitudinal axis, and proximal and distal ends;

a bladeless penetrating member adjacent the distal end of the obturator shaft;

an obturator shield mounted about the obturator shaft and having a distal shield nose, the obturator shield being adapted for longitudinal movement between an extended position where the bladeless penetrating member is substantially enclosed within the shield nose and a retracted position where the bladeless penetrating member is at least partially exposed from the shield nose;

a manually manipulative member mounted to the obturator housing and adapted for rotational movement about the longitudinal axis and relative to the obturator housing between an initial position corresponding to a first mode of operation where the obturator shield is secured in the extended position and the shield nose is usable to penetrate tissue, and a release position corresponding to a second mode of operation operatively releasing the obturator shield to permit the obturator shield to move to the retracted position thereof to expose the bladeless penetrating member for dissecting the tissue; and a control member mounted in fixed relation to the obturator housing and operatively associated with the manually manipulative member, one of the control member and the manually manipulative member including a groove and the other of the control member and the manually manipulative member including a pin, the pin traversing the groove during rotation of the manually manipulative member between the initial and release position thereof whereby terminating ends of the groove correspond to the initial and release position of the manually manipulative member.

* * * * *